United States Patent [19]

Riva

[11] 4,439,454
[45] Mar. 27, 1984

[54] PROCESS FOR CHOLINE AND VITAMIN STABILIZATION

[76] Inventor: Giuseppe Riva, Piazza Repubblica, 1, 24100 Bergamo, Italy

[21] Appl. No.: 274,001

[22] Filed: Jun. 15, 1981

[30] Foreign Application Priority Data

Jun. 24, 1980 [IT] Italy ................................. 2918 A/80

[51] Int. Cl.$^3$ .................... A61K 31/14; C07D 211/72; C07D 211/84; C07D 213/70
[52] U.S. Cl. ..................................... 424/329; 564/293
[58] Field of Search ......................... 424/329; 564/293

[56] References Cited

U.S. PATENT DOCUMENTS 3,163,579 12/1964 Derivan .............................. 424/329
3,897,485 7/1975 Meunier .............................. 424/329

OTHER PUBLICATIONS

Chemical Patents Journal 6(48), British 2-11-66, #1,047,010.

Primary Examiner—Douglas W. Robinson

[57] ABSTRACT

Process for the stabilization of choline and stabilization of vitamins, in which choline is heated with a mixture of an aldehyde and a nitrogenous compound, preferably formaldehyde and urea, and vitamins are stabilized by addition thereof to said mixture of choline, aldehyde and nitrogenous compounds before the beginning of the stabilizing reaction.

7 Claims, No Drawings

PROCESS FOR CHOLINE AND VITAMIN STABILIZATION

BACKGROUND OF THE INVENTION

1. Field of the Invention

This invention relates to a process for the stabilization of choline and stabilization of vitamins to be introduced into the starting mixture used for the stabilization of choline.

2. Prior Art

The basic importance of choline in transmethylation, as a donor of methyl units as well known; at the same time, choline operates as hepato-protective agent, preventing the accumulation of fats in the hepatic cells.

However, the use of this compound, particularly in animal feed, is restricted in that it is a highly hygroscopic liquid with all of the practical disadvantages thereby involved.

Vitamins used as supplements to human and animal foods also often require stabilization.

In order to avoid the degradation that vitamins may undergo laborious and expensive techniques are usually required and yield the desired result only for a limited period of time. It should be added that vitamins are sometimes administered together with other active elements (such as, iron, copper, zinc, etc., particularly as salts), so that it is at least desirable to limit the destabilizing action thereof on vitamins.

On the one hand, it would therefore be highly desirable to provide a process of choline stabilization by which the choline is rendered non-hygroscopic and, on the other hand, a process for vitamin stabilization, extending the effectiveness thereof over time.

Surprisingly, there has now been found a novel and unique process of chlorine stabilization in which the vitamins to be stabilized can be also introduced in the same starting mixture used for stabilization of choline. Upon reaction the vitamins thus remaining reticulated in the reaction product are preserved or protected from the effect of the destabilizing agents.

SUMMARY OF THE INVENTION

The method of this invention for stabilization of choline provides that the latter is heated with a mixture comprising an aldehyde or condensates thereof and a nitrogenous compound, particularly formaldehyde and urea, respectively.

It is also convenient to use the nitrogenous compound, such as urea, together with a mixture in turn comprising formaldehyde and urea, commercially referred to as formurea.

Surprisingly, it has been found that the foregoing reaction will also stabilize vitamins which are added to the starting compounds before the reaction begins.

The above reaction is catalyzed when the mixture is acidified with HCl.

DETAILED DESCRIPTION OF THE INVENTION

The invention will now be further described in the form of some exemplary reactions which, however, are not intended as limiting.

EXAMPLE 1

A double jacketed vessel is provided with a stirrer, and a cooling medium is circulated in the jacket of the vessel. The following mixture is placed within the vessel:

Formurea: 11.1% by weight
Urea: 11.8% by weight
(75%) Choline chloride: 77.1% by weight Formurea is a product comprising 57% formaldehyde and 23% urea, the balance being $H_2O$.

The mixture is stirred to complete dissolution of the ingredients and then a heating fluid (water) is admitted into the jacket, bringing the mass to about 70°–85° C.

In this temperature range, depending on the purity of the raw materials, the reaction is carried out and the mass suddenly solidifies.

By means of suitable expedients, the vessel is emptied and the solid mass obtained can be crumbled by a hammer mill, and then dried and milled for conversion into a non-hygroscopic, very fine powder.

EXAMPLE 2

The following components are provided:
75% Choline chloride: 74.4% by weight
Formurea: 14.88 by weight
Urea: 9.48 by weight
18.5% HCl: 1.24 by weight Choline, formurea and urea are placed in a vessel as in Example 1 and stirred for about 2 minutes at a temperature of the circulating water of about 65° C. and at a temperature of the solution in the range of 45°–50° C.

When the solution is clear because of complete dissolution of urea, the mixture is acidified with 18.5% HCl, with continued stirring.

Solidification occurs within about 60–90 seconds.

The remainder of the process is as in Example 1.

EXAMPLE 3

As in Example 1, the following starting compounds are provided:
75% Choline chloride: 32.0% by weight
Formurea: 7.1% by weight
Urea: 7.8% by weight
Vitamin complex: 53.1% by weight The vitamin complex was a mixture of vitamins A; C; $B_1 + B_6 + B_{12}$; K.

The mass solidifies while the vitamin remains reticulated by the reaction product and the vitamin complex is thus preserved or protected from effects of the destabilizing agents.

As above stated, the mass can be converted into powder or meal.

The product thus obtained is mixed with iron and potassium salts, in the suitable percentages for a correct formulation, also in powder state.

The mealy mixture is stirred to obtain a complete dispersion of the powder of metal salts in the vitamin supplement compound.

Notwithstanding the provision of such salts, the vitamins maintain their effectiveness.

EXAMPLE 4

In the course of the reaction, the product is acidified as in Example 2. The starting compounds are as follows:
75% Choline chloride: 64.40% by weight
Formurea: 14.88% by weight
Urea: 9.48% by weight
18.5% HCl: 1.24% by weight
Vitamin K (menadione): 10.00% by weight Also in this case a compact mass is obtained, in which the vitamin is reticulated and well protected over time.

The remainder of, the process is as in the preceding examples.

Of course, the ratios between the various materials may vary depending on the desired concentration of the active substance.

The basic concept is that choline can be stabilized by treatment with urea and formurea to avoid the hygroscopic phenomenum, a vitamin supplement can be introduced into the starting mixture, the vitamin remaining entrapped within the protective reticle of the reaction product, thus retaining its activity and characteristics for an extended period.

What is claimed is:

1. A process for stabilizing choline by preparing a non-hygroscopic form thereof, comprising the steps of:
   (a) forming a reaction mixture containing about 32–77.1% by weight choline chloride, about 7.1–14.88% by weight formurea and about 7.8–11.8% by weight urea;
   (b) adding from 0% to about 53% by weight of a vitamin supplement;
   (c) heating the reaction mixture to about 45°–85° C.; and
   (d) adding from 0% to about 1.24% by weight of 18.5% hydrochloric acid to said reaction mixture; whereby said reaction mixture forms a solidified reaction product.

2. The process of claim 1, wherein 1.24% by weight 18.5% hydrochloric acid is added to said reaction mixture while heating said reaction mixture to a temperature in the range of about 45° to 50° C.

3. The process of claim 1, wherein said reaction mixture is heated to a temperature in the range of about 75° to 85° C.

4. The process of claim 1, wherein said vitamin supplement is selected from the group consisting of vitamins A, C, B1, B6, B12 and K, and combinations thereof, and is added to said reaction mixture prior to heating, said vitamin supplement comprising 10% to about 53% by weight of the total mixture, whereby said vitamin supplement is stabilized in said solidified reaction product.

5. The process of claim 2, wherein said vitamin supplement is selected from the group consisting of vitamins A, C, B1, B6, B12 and K, and combinations thereof, and is added to said reaction mixture prior to heating, said vitamin supplement comprising 10% to about 53% by weight of the total mixture, whereby said vitamin supplement is stabilized in said solidified reaction product.

6. The process of claim 4, further including the steps of pulverizing said solidified reaction product to a powder, and mixing said powder with iron and potassium salts.

7. The process of claim 5, further including the steps of pulverizing said solidified reaction product to a powder, and mixing said powder with irion and potassium salts.

* * * * *